United States Patent
Akerfeldt et al.

(10) Patent No.: US 10,758,263 B2
(45) Date of Patent: Sep. 1, 2020

(54) MEDICAL DEVICE

(71) Applicant: APRIOMED AB, Uppsala (SE)

(72) Inventors: Dan Akerfeldt, Knivsta (SE); Afshin Gangi, Strasbourg (FR)

(73) Assignee: APRIOMED AB, Uppsala (SE)

( * ) Notice: Subject to any disclaimer, the term of this patent is extended or adjusted under 35 U.S.C. 154(b) by 0 days.

(21) Appl. No.: 15/511,357

(22) PCT Filed: Sep. 15, 2015

(86) PCT No.: PCT/EP2015/071014
§ 371 (c)(1),
(2) Date: Mar. 15, 2017

(87) PCT Pub. No.: WO2016/041921
PCT Pub. Date: Mar. 24, 2016

(65) Prior Publication Data
US 2017/0245887 A1      Aug. 31, 2017

(30) Foreign Application Priority Data
Sep. 18, 2014   (EP) ..................................... 14185410

(51) Int. Cl.
*A61B 17/34* (2006.01)
*A61M 25/01* (2006.01)
(Continued)

(52) U.S. Cl.
CPC ...... *A61B 17/3421* (2013.01); *A61B 17/3474* (2013.01); *A61M 25/0102* (2013.01);
(Continued)

(58) Field of Classification Search
CPC ............ A61B 17/3421; A61B 17/3474; A61B 2090/0811; A61B 2017/347; A61M 39/12; A61M 25/065; A61M 25/0102
See application file for complete search history.

(56) References Cited

U.S. PATENT DOCUMENTS 5,104,381 A * 4/1992 Gresl ................. A61B 1/00135
                                                         604/158
5,312,363 A * 5/1994 Ryan .................. A61B 17/3496
                                                         137/846
(Continued)

FOREIGN PATENT DOCUMENTS

CN            201426759 Y       3/2010
WO         WO-97/43958 A1       11/1997
(Continued)

OTHER PUBLICATIONS

Japanese Office Action and English translation, Application No. 2017-506999, dated May 28, 2019, 14 pages.
(Continued)

*Primary Examiner* — Amber R Stiles
(74) *Attorney, Agent, or Firm* — Foley & Lardner LLP (57) ABSTRACT

A medical device is disclosed comprising an elongated needle assembly having a distal end, a proximal end and a longitudinal axis A, the needle assembly comprises a tubular cannula having a sharpened distal end, a proximal cannula portion, and a longitudinal bore along the longitudinal axis A, and a stylet configured to extend through the bore of the cannula, and having a blunt distal end and a proximal stylet portion. The needle assembly is provided with a spring member configured to urge the stylet in a distal direction along the longitudinal axis, such that the stylet is axially spring-biased in said distal direction. The medical device further comprises a connecting member configured to detachably attach said stylet to said cannula, wherein said stylet is configured to be attached to the tubular cannula by the connecting member such that the blunt distal end protrudes just beyond the sharpened distal end of the cannula when no force is applied to the distal end of the stylet in a proximal direction along said longitudinal axis, and wherein the connecting member is configured to enable detachment
(Continued)

of the proximal portions from each other such that the stylet may be fully withdrawn from the longitudinal bore.

16 Claims, 3 Drawing Sheets

(51) Int. Cl.
*A61M 25/06* (2006.01)
*A61M 39/12* (2006.01)
*A61B 90/00* (2016.01)

(52) U.S. Cl.
CPC .......... *A61M 25/065* (2013.01); *A61M 39/12* (2013.01); *A61B 2017/347* (2013.01); *A61B 2090/0811* (2016.02)

(56) References Cited

U.S. PATENT DOCUMENTS

| | | | | |
|---|---|---|---|---|
| 5,320,608 A | * | 6/1994 | Gerrone | A61B 17/3417 604/117 |
| 5,685,852 A | | 11/1997 | Trukel et al. | |
| 2003/0130621 A1 | * | 7/2003 | Bryan | A61B 17/3401 604/164.01 |
| 2004/0260199 A1 | | 12/2004 | Hardia, Jr. et al. | |
| 2016/0022312 A1 | * | 1/2016 | Tang | A61B 17/3474 604/506 |

FOREIGN PATENT DOCUMENTS

| | | |
|---|---|---|
| WO | WO-03/057282 A1 | 7/2003 |
| WO | WO-2009/091567 A1 | 7/2009 |
| WO | WO 2013/173617 A1 | 11/2013 |
| WO | WO 2014/028428 A1 | 2/2014 |

OTHER PUBLICATIONS

Chinese Office Action and English translation, Application No. 201580042492.3, dated Nov. 1, 2019, 20 pages.

* cited by examiner

MEDICAL DEVICE

FIELD OF THE INVENTION

The present invention relates to a medical device according to the preamble of the independent claim.

Generally the invention relates to the medical field of minimally invasive diagnostic and treatment instruments and methods. In particular it relates to needles or cannulas providing an access to tissue e.g. for sampling, measuring, treating and surgical purposes.

BACKGROUND OF THE INVENTION

When inserting a needle through tissue e.g. for sampling of an organ the needle often must be pushed through tissue having different inserting resistance due to different softness of the tissue.

A so-called Veress needle is a special needle used in laparoscopic surgical procedures. A conventional Veress needle consists of a hollow outer cannula ground obliquely to a sharp point at a distal end, and terminating in a plastic housing at the opposite proximal end. Enclosed within the outer cannula is a hollow tube that has a blunt tip at its distal end (common to the sharp tip of the outer cannula), and that is axially spring-biased in a distal direction by a spring contained in the plastic housing. When no force is applied to the distal end to resist the penetrating point, the spring bias forces the hollow inner tube to protrude just beyond the sharp tip of the outer cannula, obscuring the sharp tip and thereby protecting underlying organs from damage. When a force which overcomes the spring bias is applied to its distal end, as when the Veress needle is being pushed through a patient's abdominal wall, the inner tube is driven back within the outer cannula, exposing the sharp needle tip.

In the following, for illustrative purposes a few examples of documents within the field of Veress needles are cited.

WO-2013/173617 relates to a medical device encompassing a Veress needle with a mechanism for optionally extending, locking and unlocking its central tubular stylet.

In WO-2014/028428 a Veress needle is disclosed including an outer needle having a shaft and a sharp distal point. The sharp distal point and a distal portion of the shaft are configured to penetrate tissue. A spring-loaded, inner cannula is disposed in the outer needle. The cannula has a dull tip and a gas exit aperture is formed near a distal end of the cannula. The outer needle has an outwardly expandable portion located on the distal portion of the shaft.

Thus, one central feature of the Veress needle is that when the needle assembly penetrates soft tissue the stylet is in its distal position due to the spring-bias from the spring member. Thereby the tissue is less harmed because the blunt distal end is in its distal position "protecting" the sharp distal end of the cannula.

Other types of needle assemblies have been described that also use spring-biased members. One such assembly is described in US Patent Application 2003/0130621A1, which discloses a spinal needle system for entry into the epidural space. Another assembly is described in U.S. Pat. No. 5,685,852, which shows a needle assembly for epidural access comprising a hollow outer cannula with a sharp distal tip and a hollow blunt-ended stylet mounted within the cannula such that it is spring-biased to extend distally of the outer cannula.

Based upon the general knowledge of the Veress needle and other needle assemblies the inventor has identified further applications of the technique.

The object of the present invention is to achieve an improved needle assembly in the sense that it may be applied for different purposes and configured to be used in tissue having different properties.

In addition the needle assembly relieves the patient discomfort in that less manipulation is required when performing standard procedures.

SUMMARY OF THE INVENTION

The above-mentioned object is achieved by the present invention according to the independent claim. Preferred embodiments are set forth in the dependent claims.

The present invention relates to a releasable spring-biased stylet configured to be detachably attached to a tubular cannula by a connecting member.

A medical device is disclosed comprising an elongated needle assembly having a distal end, a proximal end and a longitudinal axis A, the needle assembly comprises a tubular cannula having a sharpened distal end, a proximal cannula portion, and a longitudinal bore along the longitudinal axis A, and a stylet configured to extend through the bore of the cannula, and having a blunt distal end and a proximal stylet portion. The needle assembly is provided with a spring member configured to urge the stylet in a distal direction along the longitudinal axis, such that the stylet is axially spring-biased in said distal direction. The medical device further comprises a connecting member configured to detachably attach said stylet to said cannula, wherein said stylet is configured to be attached to the tubular cannula by the connecting member such that the blunt distal end protrudes just beyond the sharpened distal end of the cannula when no force is applied to the distal end of the stylet in a proximal direction along said longitudinal axis, and wherein the connecting member is configured to enable detachment of the proximal portions from each other such that the stylet may be fully withdrawn from the longitudinal bore.

The needle assembly is thus adapted to the varying properties of different types of tissues, while at the same time allowing for tissue sampling and other procedures to be performed at a specific target site. In particular, when the blunt end of the stylet is most distal, the insertion through tissue for reaching the target position results in less influence on tissue being passed.

When the distal part of the needle assembly has reached its target position the stylet may be fully withdrawn and an optional medical instrument may be inserted into the longitudinal bore of the needle in order e.g. to perform a biopsy sampling procedure or other medical procedure. This aspect relieves the patient discomfort in that less manipulation is required when performing standard procedures, e.g. tissue sampling.

DETAILED DESCRIPTION OF PREFERRED EMBODIMENTS OF THE INVENTION

With references to the appended figures the present invention will now be described in detail.

Throughout the figures the same, or similar items, have the same reference signs. Notably, the term "distal" herein refers to a direction or part located away from a user, and in the case of the present disclosure, refers to a part of a medical device to be inserted furthest into a subject. The term "proximal" thus refers to the opposite direction or parts, such as a part of a medical device closest to a user and outside the body of a subject.

Figure 1:
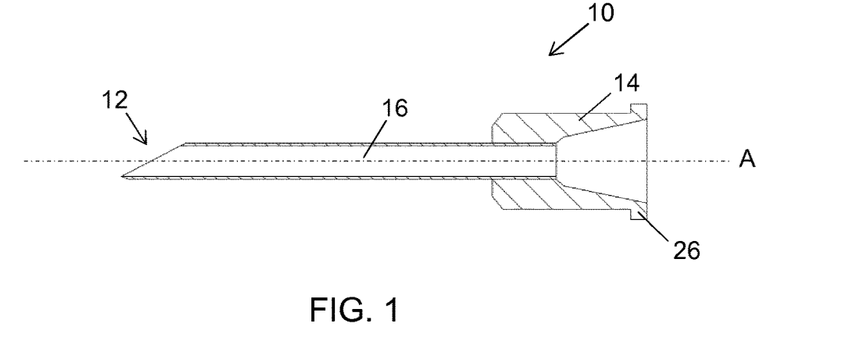
FIG. 1 illustrates a cross-sectional side-view of a cannula.
Figure 2:
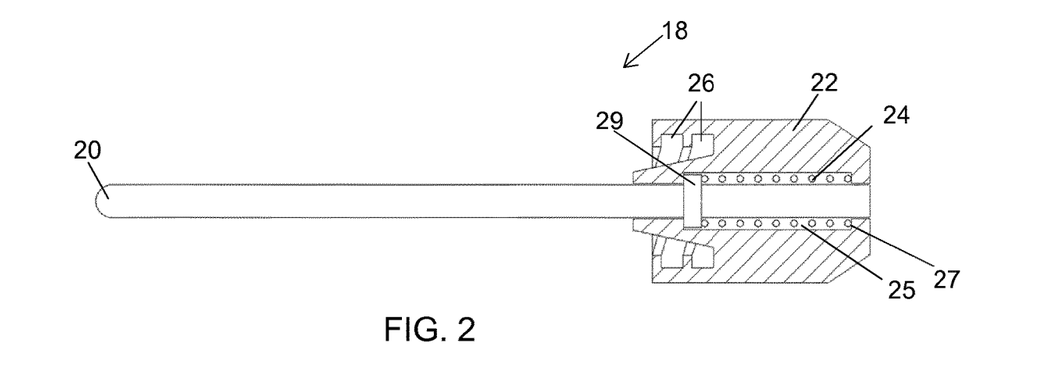
FIG. 2 illustrates a cross-sectional side-view of a stylet.
Figure 3:
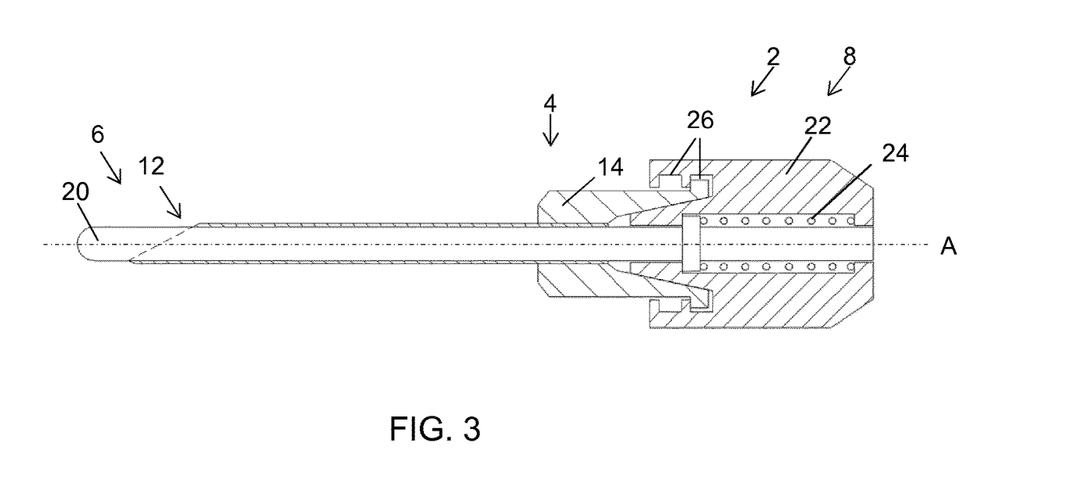
FIG. 3 illustrates a cross-sectional side-view of a needle assembly.

First with references to FIG. 3 a medical device 2 comprises an elongated needle assembly 4 having a distal end 6, a proximal end 8 and a longitudinal axis A. The needle assembly comprises a tubular cannula 10 which is illustrated in FIG. 1, and a stylet 18 which is illustrated in FIG. 2.

The tubular cannula 10 (see FIG. 1) is provided with a sharpened distal cutting end 12, a proximal cannula portion 14, and a longitudinal bore 16 along the longitudinal axis A. Notably, the term "sharpened distal cutting end" of a cannula herein means that the cannula is provided with a slanted distal end ending in a distal sharp point. The distal circumferential edge of the cannula wall is sharp enough to allow the cannula to penetrate smoothly into and through tissue. Such a cannula may be used to collect a tissue sample in the longitudinal bore by cutting a tissue sample using the circumferential sharp distal edge. It may also be used for access to a specific target site for any procedure in which a medical instrument can be in inserted through the cannula to reach the desired target site.

The cannula is preferably made from a metal tube having an outer diameter in the range of 0.5 mm-5.0 mm and an inner diameter in the of range of 0.4 mm-4.9 mm. The proximal cannula portion 14 is preferably made from a suitable plastic material that e.g. is fastened to the tube by an appropriate adhesive or by a melting procedure. The proximal cannula portion has a proximal widening opening configured to receive a mating portion of the stylet which will be further discussed below. The opening leads into and gives access to the longitudinal bore 16 from the proximal direction. In addition a connecting member 26 is provided at the proximal portion.

Figure 6:
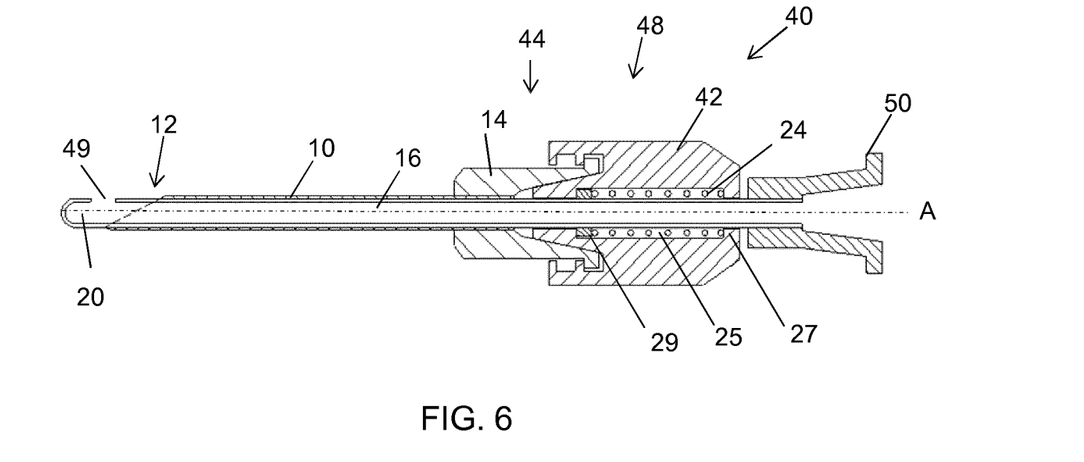
FIG. 6 illustrates a cross-sectional side-view of a stylet.
Figure 7:
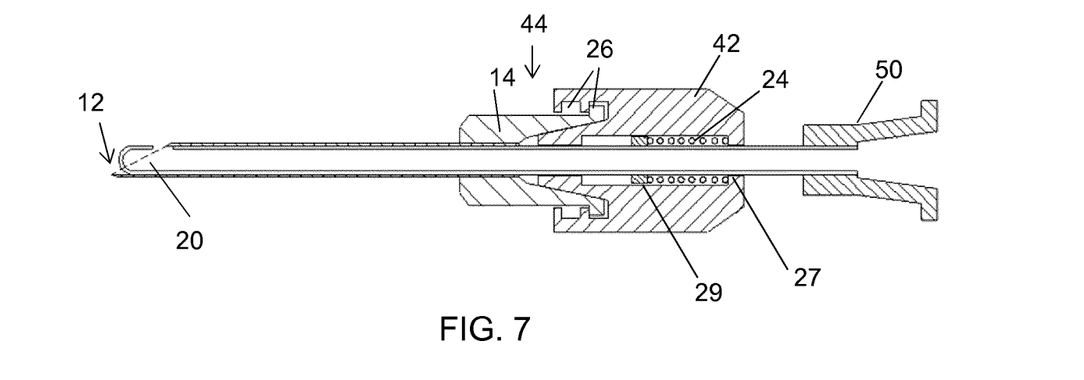
FIG. 7 illustrates a cross-sectional side-view of a stylet.

A stylet 18 (see FIG. 2) is configured to extend through the bore 16 of the cannula 10, and is provided with a blunt distal end 20 and a proximal stylet portion 22. The stylet 18 may be a solid rod made from metal or a suitable plastic. The stylet may also be a hollow tube made from metal or a suitable plastic with a blunt closed distal end and an opening on one side close to the distal end. The latter alternative is shown in FIGS. 6 and 7, and will be described further below.

The inner diameter of said longitudinal bore 16 is slightly larger than the outer diameter of the stylet 18 allowing the stylet to smoothly be moved in relation to the cannula 10 along the longitudinal axis A.

Furthermore, the needle assembly 4 is provided with a spring member 24 configured to urge the stylet in a distal direction along the longitudinal axis, such that the stylet is axially spring-biased in the distal direction. In FIG. 2 the spring member is illustrated as a helix-wound spring wound around a proximal part of the stylet rod in a spring member chamber 25. The chamber is provided with a proximal wall or protrusion 27 for taking up forces exerted by the proximal end of the spring member 24. The distal end of the spring member 24 cooperates with a distal support member 29 fixated to the stylet rod.

In the figures the spring member is embodied by a helix spring, but of course the spring member 24 may also be embodied by any other alternative elastic component, e.g. made from a suitable elastic plastic material.

As is seen in e.g. FIG. 2, the medical device further comprises a connecting member 26 configured to detachably attach the stylet 18 to the cannula 10. The assembled medical device is illustrated in FIG. 3. More specifically, the stylet 18 is configured to be attached to the tubular cannula 10 by a connecting member 26 such that the blunt distal end 20 protrudes just beyond the sharpened distal end 12 of the cannula 10 when no force is applied to the distal end of the stylet in a proximal direction along said longitudinal axis, as illustrated in e.g. FIG. 3.

The expression just beyond is related to the dimension, e.g. the diameter of the cannula, and may in some examples be in the order of some millimetres, i.e. enough to appropriately protect the sharpened distal end such that surrounding tissue not is harmed during insertion.

The connecting member 26 is configured to enable detachment of the proximal portions 14, 22 from each other such that the stylet 18 may be withdrawn from the longitudinal bore 16. Furthermore, the connecting member 26 is configured to detachably fixate the proximal portions 14, 22 to each other such that relative axial movement of the proximal portions along the longitudinal axis A is prevented.

The connecting member 26 may comprise a screw connection, i.e. a threaded connection, to fixate the proximal portions to each other, which is illustrated by the figures. In such an assembly the proximal cannula portion 14 is provided with external threads being a part of the connecting member 26 and the proximal stylet portion 22 is provided with internal threads also being a part of the connecting member 26.

As an alternative the connecting member 26 instead comprises a bayonet connection to fixate the proximal portions to each other.

Thus, in accordance with the present disclosure, when the blunt distal end 20 is subjected to a force higher than a predetermined value in a proximal direction along said longitudinal axis, the stylet 18 is driven back within the longitudinal bore 16, exposing the sharpened distal end 12 of the cannula 10. This procedure is illustrated by FIGS. 4 and 5.

Figure 4:
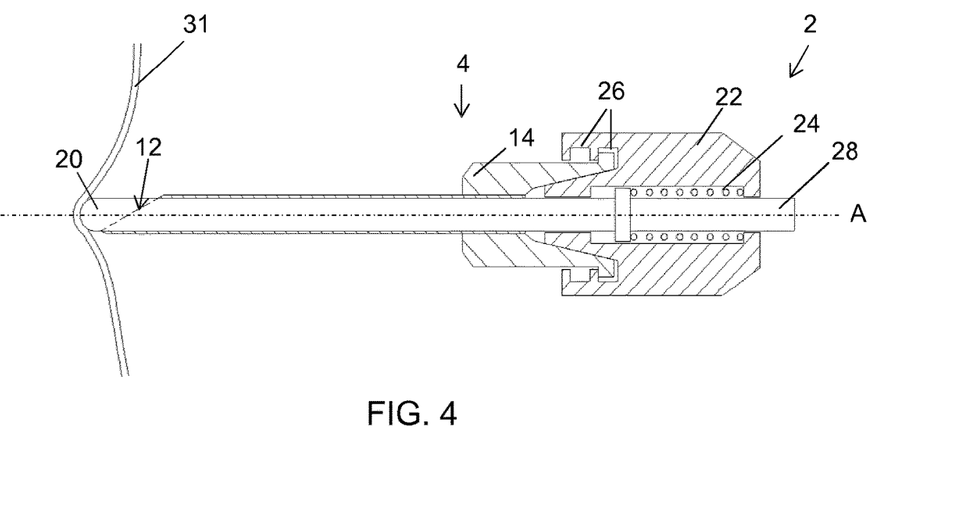
FIG. 4 illustrates a cross-sectional side-view of a needle assembly, during use.

In FIG. 4 the blunt end 20 is subjected to a force having a direction along the proximal direction along the axis A. The force may occur e.g. when the blunt end comes into contact with harder tissue 31, e.g. a bone structure or other firm tissue. The stylet is then moved in the proximal direction against the force exerted by the spring member 24.

Figure 5:
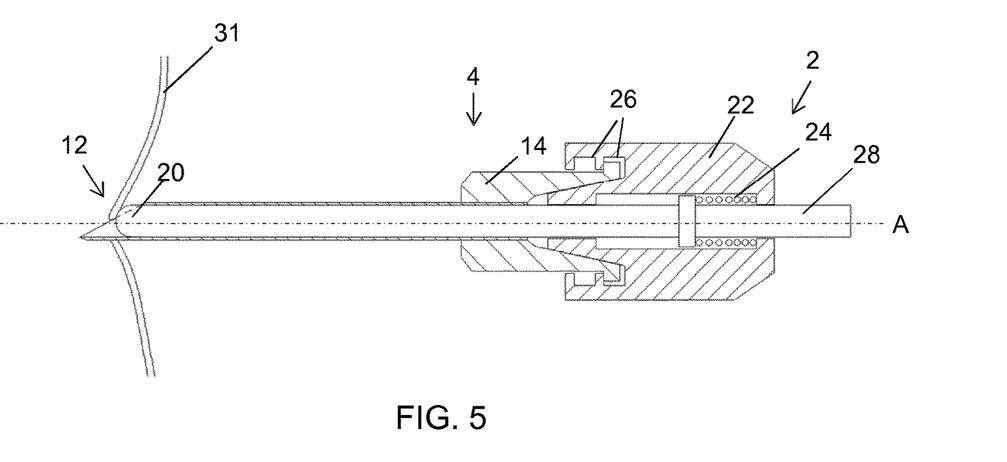
FIG. 5 illustrates a cross-sectional side-view of a needle assembly, during use.

When the proximally directed force is higher than a predetermined value the sharpened distal end 12 is exposed, which is illustrated by FIG. 5, and the sharpened distal end 12 may then penetrate the harder tissue 31.

The predetermined value is related to the nature of the harder tissue, and may be varied by using a softer or harder spring member. If a softer spring member is applied less force is required in order to expose the sharpened distal end and correspondingly if a harder spring member is applied a higher force is required in order to expose the sharpened distal end.

In particular during the insertion procedure, the blunt distal end 20 of the stylet prevents tissue from entering the distal opening of the longitudinal bore 16.

During use it is advantageous to receive an indication of the nature, i.e. the softness, of the tissue the needle assembly is inserted into.

In order to indicate the nature of the tissue, the connecting member 26 is preferably provided with an indicator 28 configured to indicate the axial position of the stylet 18 in relation to the cannula 10, when the stylet is attached to the cannula by the connecting member. In FIGS. 4 and 5 the indication member is realised by allowing a proximal end of the stylet rod to protrude through the proximal end of the proximal stylet portion 22 when a force along the longitudinal axis exists. Thereby the axial position of the stylet in relation to the cannula is indicated. The length of the protruding proximal end of the stylet rod is linearly dependent on the force in the longitudinal axis. This in turn may give valuable information of the nature of the tissue that the distal end of the needle assembly passes during insertion.

Notably, an indicator 28 can thus be visually observed by a user as protruding from the proximal end of the proximal stylet portion 22 when a force along the longitudinal axis exists. In other words, a visual indicator 28 is configured such that a change in axial position of the stylet 18 in relation to the cannula 10 is visually observed by a user, i.e. a visual indicator may be any structure whose relative position and movement may be observed by a user during use. A visual indicator could be e.g. a button, lever or other structure.

The stylet proximal portion may be provided with a transparent window (not shown) configured such that an indication mark, e.g. a colour mark, at the stylet rod may be identified through the window. The position of the colour mark gives an indication of the relative position of the stylet and the cannula.

In addition to visual indication, or as an alternative, the needle assembly can be configured such that the indicator 28 provides a tactile indication to a user, indicating a force in a proximal direction, i.e. that a harder tissue has been reached by the distal end of the needle assembly, and the longitudinal force is pushing back the blunt distal end of the stylet 18, exposing the sharp distal end of the cannula. A needle assembly providing tactile indication can be designed such that, during use of the assembly, a user holds a finger or thumb over the site where the indicator 28 will protrude proximally when a proximal force is exerted on the stylet. Thus, the user will then immediately feel the indicator against a finger or thumb when it is pushed out of the proximal stylet portion 22.

In other words, a tactile indicator is configured such that a change in axial position of the stylet 18 in relation to the cannula 10 is tactilely sensed by a user, i.e. a tactile indicator may be any structure whose relative position and movement may be felt by a user's hand, e.g. finger or thumb, during use. A tactile indicator could be e.g. a button, lever or other structure.

FIGS. 6 and 7 show another needle assembly 44, wherein the needle assembly 44 comprises a cannula 10 and a stylet 48. Herein the cannula 10 is as described above, i.e. is provided with a sharpened distal end 12, a proximal cannula portion 14, and a longitudinal bore 16 along the longitudinal axis A. The proximal cannula portion 14 is provided with a connecting member 26.

The stylet 48 comprises a blunt distal end 20 and a proximal stylet portion 42, and is configured to extend through the bore 16 of the cannula 10. In this assembly, the stylet 48 is a hollow tube with a blunt closed distal end 20 and an opening 49 on one side close to the distal end 20. The opening 49 allows access from the inner lumen of the stylet 48 to the surrounding space outside the needle assembly. The use of such a hollow stylet 48 and configuration of the opening 49 will be described below.

As is previous assemblies, the needle assembly 44 is provided with a spring member 24 configured to urge the stylet in a distal direction along the longitudinal axis, such that the stylet is axially spring-biased in the distal direction. In FIGS. 6 and 7 the spring member is illustrated as a helix-wound spring wound around a proximal part of the stylet rod in a spring member chamber 25. The chamber is provided with a proximal wall or protrusion 27 for taking up forces exerted by the proximal end of the spring member 24. The distal end of the spring member 24 cooperates with a distal support member 29 fixated to the stylet. Notably, other types of spring members can be used, as long as they can bias the stylet 48 in the desired direction.

Also similar to previous assemblies described above, the stylet 48 is configured to be attached to the tubular cannula 10 by the connecting member 26 such the blunt distal end 20 protrudes just beyond the sharpened distal end 12 of the cannula 10 when no force is applied to the distal end of the stylet in a proximal direction along said longitudinal axis. As illustrated in FIG. 6, the opening 49 is preferably located within the distal part of the stylet 48 which protrudes just beyond the sharpened distal end 12 of the cannula 10 when no force is applied to the distal end of the stylet in a proximal direction along said longitudinal axis. As an example, the opening 49 may be located within a few millimeters of the blunt distal end of the stylet 48. The opening 49 is preferably between approximately 0.5 to 3 mm wide.

The connecting member 26 is configured to enable detachment of the proximal portions 14, 42 from each other such that the stylet 48 may be withdrawn from the longitudinal bore 16. Furthermore, the connecting member 26 is configured to detachably fixate the proximal portions 14, 42 to each other such that relative axial movement of the proximal portions along the longitudinal axis A is prevented.

During use, the needle assembly 44 is inserted through tissue towards e.g. a desired target site. Due to the spring-biased configuration of the stylet's relative position the blunt end 20 will protrude from the cannula 10 and minimize any tissue damage during insertion.

Once the desired target site is reached, a hydrodissection technique can be used to dissect or separate tissue, due to the hollow stylet 48. Hydrodissection uses a pressurized stream of a fluid, i.e. gas or liquid, for instance physiological saline. Hydrodissection is used to separate different organs or types of tissue prior to a procedure, primarily to protect such non-target tissue from any damage or unwanted effects from the procedure to be performed. An example is to move intestines away from an internal organ before ablation, thereby ensuring that the intestines are not subjected to the heat of ablation.

To use hydrodissection with the present needle assembly 44, a user connects a flow of fluid via e.g. a tube to a fluid connector 50 at the proximal end of the stylet 48. The fluid connector 50 may be e.g. a luer-lock, a threaded connector, a friction based connector or other suitable fluid connector. During initial penetration of soft tissue or once a desired target site has been reached, and when the needle assembly is in the configuration shown in FIG. 6, the fluid will flow distally through the stylet in the inner lumen and exit the device through the opening 49 near the distal end, which will provide gentle separation of tissue. Notably, even though the stylet is this embodiment is hollow, it can be used without hydrodissection, and will then function just as the solid stylet described above.

As previously described, when the blunt distal end 20 is subjected to a force higher than a predetermined value in a proximal direction along said longitudinal axis, the stylet 48 is driven back within the longitudinal bore 16, exposing the sharpened distal end 12 of the cannula 10. This procedure is illustrated by FIGS. 6 and 7. A force having a direction along the proximal direction along the axis A may occur e.g. when the blunt end comes into contact with harder tissue, e.g. a bone structure or a firmer organ, as previously described in connection with FIG. 4. The stylet is then moved in the proximal direction against the force exerted by the spring member 24, as shown in FIG. 7, wherein the spring 24 is compressed.

When the proximally directed force is higher than a predetermined value the sharpened distal end 12 is exposed, which is illustrated by FIG. 7, and the sharpened distal end 12 may then penetrate the harder tissue. The predetermined value can be adapted to different tissue types by adapting the configuration and type of spring member, as described above.

The fluid connector 50, or other part of the proximal end of the stylet 48, may also function as an visual indicator, and optionally a tactile indicator, of the relative longitudinal position between the stylet 48 and the cannula 10, as it may be visually observed (and optionally may be tactilely sensed) by a user as protruding a certain distance from the proximal end of the proximal stylet portion 42 when a force along the longitudinal axis exists. In addition, or as an alternative, a separate tactile indicator may be provided at a proximal end of the proximal stylet portion 42. Such a tactile indicator, being either the fluid connector 50 or a separate part, is configured such that a change in axial position of the stylet 48 in relation to the cannula 10 is tactilely sensed by a user, i.e. a tactile indicator is any structure whose relative position and movement may be felt by a user's hand, e.g. finger or thumb, during use. A tactile indicator could be e.g. a button, lever or other structure.

In any of the above described embodiments, the proximally directed force can be temporarily counteracted by a user pressing or pushing in a distal direction on a proximal end of the needle assembly, such as either on the indicator 28 (FIGS. 4 and 5) or on the fluid connector 50 (FIGS. 6 and 7) or another part of the proximal end of the stylet. This will hold the stylet 18, 48 in a position wherein the blunt distal tip 20 extends fully out of the sharp distal tip of the cannula 10. Using such a function gives the user an option to keep the blunt distal stylet end 20 in the most distal position, even though a harder tissue is reached. This function is advantageous in e.g. situations when it is desired to manipulate a specific tissue structure with the tip of the assembly without risking tissue damage. An example to illustrate this feature is to, during insertion towards an internal organ in the abdomen, move intestines out of the way with the blunt distal tip of the assembly. Thereby the risk of damaging the intestinal tissue is minimized.

In any of the above described embodiments, the entire stylet and/or cannula or parts of the assembly, may be made of such material which is visible in common imaging techniques, such as X-ray or CT imaging. This is advantageous in that the assembly, or parts of it, such as the tip of the stylet and/or tip of the cannula, may be observed in real-time using such imaging techniques during a procedure.

When the needle assembly 4,44 has been inserted and reached a target lesion 30 (see FIG. 8), from which a sample is desired or another procedure is to be performed, the stylet may be completely removed in from the cannula 10. This is applicable both when the stylet is a solid rod and when the stylet is hollow. Thus, it is useful to be able to remove the stylet 18, 48, such that access is gained via the tubular bore 16 of the cannula 10 to the target lesion 30.

Figure 8:
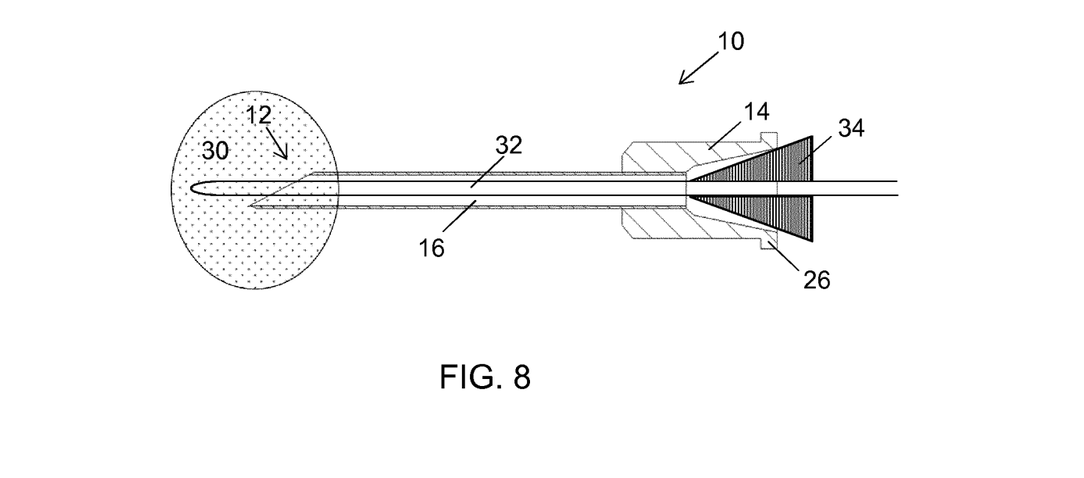
FIG. 8 illustrates a cross-sectional side-view of a cannula, during use.

The cannula 10 may be configured to receive a medical instrument 32 in the longitudinal bore when the stylet 18, 48 is fully withdrawn from the longitudinal bore 16. The medical instrument 32 may e.g. be a biopsy sampling device.

The connecting member 26 is preferably configured to cooperate with a coupling member 34 of the medical instrument. In the example of FIG. 8 the coupling member is illustrated as being cone-, or wedge-shaped configured to cooperate with the connecting member 26 by a frictional fit.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:
1. A medical device comprising:
an elongated needle assembly having a distal end, a proximal end and a longitudinal axis A, the needle assembly comprising
a tubular cannula having a sharpened distal end, a proximal cannula portion, and a longitudinal bore in the tubular cannula along the longitudinal axis, the sharpened distal end comprising a slanted distal end terminating in a sharpened distal point,
a stylet configured to extend through the bore of the tubular cannula, and having a blunt distal end and a proximal stylet portion, the stylet comprising a stylet rod, and
a spring member configured to urge the stylet in a distal direction along the longitudinal axis, such that the stylet is axially spring-biased in the distal direction,
an indicator, and
a connecting member configured to detachably attach the stylet to the tubular cannula, wherein
the stylet is configured to be attached to the tubular cannula by the connecting member such that the blunt distal end protrudes just beyond the sharpened distal end of the tubular cannula when no force is applied to the distal end of the stylet in a proximal direction along the longitudinal axis,
the connecting member is configured to enable detachment of the proximal cannula portion and the proximal stylet portion from each other such that the stylet is configured to be fully withdrawn from the longitudinal bore,
the indicator is configured to indicate an axial position of the stylet in relation to the tubular cannula when the stylet is attached to the tubular cannula by the connecting member,
the indicator comprises
a visual indicator configured such that a change in axial position of the stylet in relation to the tubular cannula may be visually observed by a user by observing the visual indicator, and
a tactile indicator configured such that a change in axial position of the stylet in relation to the tubular cannula is tactilely sensed by a user via the tactile indicator,
the indicator is a proximal end of the stylet rod, and
the indicator is structured such that only when a force is applied to the distal end of the stylet in the proximal direction along the longitudinal axis, the proximal end of the stylet rod is configured to protrude from a proximal end of the proximal stylet portion, the indicator is configured to be in a first position when a force is applied to the distal end of the stylet in the proximal direction along the longitudinal axis, and in a second position when the force is not applied to the distal end of the stylet in the proximal direction along the longitudinal axis, in the first position, the indicator protrudes from the proximal end of the proximal stylet portion, and the indicator is exposed to a finger or thumb of the user such that the indicator is disposed to interact with the finger or thumb of the user, and in the second position, the indicator is contained in the proximal stylet portion.

2. The medical device according to claim 1, wherein the connecting member is configured to detachably fix the proximal cannula portion and the proximal stylet portion to each other such that relative axial movement of the proximal cannula portion and the proximal stylet portion along the longitudinal axis is prevented.

3. The medical device according to claim 1, wherein when the blunt distal end is subjected to a force higher than a predetermined value in a proximal direction along the longitudinal axis, the stylet is driven back within the longitudinal bore exposing the sharpened distal end of the tubular cannula.

4. The medical device according to claim 1, wherein an inner diameter of the longitudinal bore is slightly larger than an outer diameter of the stylet such that the stylet is configured to smoothly be moved in relation to the tubular cannula.

5. The medical device according to claim 1, wherein the stylet rod comprises a solid rod.

6. The medical device according to claim 1, wherein the stylet is hollow and comprises an opening adjacent to the blunt distal end, the opening allowing access to an inner lumen of the stylet.

7. The medical device according to claim 6, wherein the opening is located within a distal part of the stylet that protrudes just beyond the sharpened distal end of the tubular cannula when no force is applied to the distal end of the stylet in the proximal direction along the longitudinal axis.

8. The medical device according to claim 6, wherein the stylet further comprises a fluid connector at the proximal end of the stylet rod, the fluid connector being configured to connect the inner lumen of the hollow stylet to a fluid source.

9. The medical device according to claim 1, wherein the tubular cannula is configured to receive a medical instrument in the longitudinal bore when the stylet is withdrawn from the longitudinal bore.

10. The medical device according to claim 9, wherein the connecting member is configured to cooperate with the medical instrument.

11. The medical device according to claim 1, wherein in the second position, an entirety of the indicator is contained in the proximal stylet portion.

12. The medical device according to claim 1, wherein the indicator is configured to be in the second position when no force is applied to the distal end.

13. The medical device according to claim 1, wherein in the second position, a proximal most end of the stylet rod is flush with the proximal stylet portion.

14. The medical device of claim 1, wherein the indicator is an outermost proximal part of the stylet rod.

15. A medical device comprising:
an elongated needle assembly having a distal end, a proximal end and a longitudinal axis A, the needle assembly comprising
a tubular cannula having a sharpened distal end, a proximal cannula portion, and a longitudinal bore in the tubular cannula along the longitudinal axis, the sharpened distal end comprising a slanted distal end terminating in a sharpened distal point,
a stylet configured to extend through the bore of the tubular cannula, and having a blunt distal end and a proximal stylet portion, the stylet comprising a stylet rod, and
a spring member configured to urge the stylet in a distal direction along the longitudinal axis, such that the stylet is axially spring-biased in the distal direction,
an indicator, and
a connecting member configured to detachably attach the stylet to the tubular cannula,
wherein
the stylet is configured to be attached to the tubular cannula by the connecting member such that the blunt distal end protrudes just beyond the sharpened distal end of the tubular cannula when no force is applied to the distal end of the stylet in a proximal direction along the longitudinal axis,
the connecting member is configured to enable detachment of the proximal cannula portion and the proximal stylet portion from each other such that the stylet is configured to be fully withdrawn from the longitudinal bore,
the indicator is configured to indicate an axial position of the stylet in relation to the tubular cannula when the stylet is attached to the tubular cannula by the connecting member,
the indicator is configured to
provide a visual indication such that a change in axial position of the stylet in relation to the tubular cannula may be visually observed by a user by observing the indicator, and
provide a tactile indication such that a change in axial position of the stylet in relation to the tubular cannula is tactilely sensed by a user via the indicator,
the indicator is a proximal end of the stylet rod, and
the indicator is structured such that
only when a force is applied to the distal end of the stylet in the proximal direction along the longitudinal axis, the proximal end of the stylet rod is configured to protrude from a proximal end of the proximal stylet portion,
the indicator is configured to be in a first position when a force is applied to the distal end of the stylet in the proximal direction along the longitudinal axis, and in a second position when the force is not applied to the distal end of the stylet in the proximal direction along the longitudinal axis,
in the first position, the indicator protrudes from the proximal end of the proximal stylet portion, and the indicator is exposed to a finger or thumb of the user such that the indicator is disposed to interact with the finger or thumb of the user, and in the second position, the indicator is contained in the proximal stylet portion.

16. The medical device of claim 15, wherein the indicator is an outermost proximal part of the stylet rod.

* * * * *